United States Patent
Gade et al.

(10) Patent No.: US 9,048,438 B2
(45) Date of Patent: Jun. 2, 2015

(54) TETRAAZAPEROPYRENE COMPOUNDS AND THEIR USE AS N-TYPE SEMICONDUCTORS

(75) Inventors: Lutz Gade, Nussloch (DE); Susanne Martens, Loerrach (DE); Sonja Geib, Dossenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/005,449

(22) PCT Filed: Mar. 2, 2012

(86) PCT No.: PCT/IB2012/050990
§ 371 (c)(1),
(2), (4) Date: Sep. 16, 2013

(87) PCT Pub. No.: WO2012/123848
PCT Pub. Date: Sep. 20, 2012

(65) Prior Publication Data
US 2014/0005390 A1    Jan. 2, 2014

Related U.S. Application Data

(60) Provisional application No. 61/452,675, filed on Mar. 15, 2011.

(51) Int. Cl.
| | |
|---|---|
| C07D 487/22 | (2006.01) |
| H01L 51/00 | (2006.01) |
| C07D 487/06 | (2006.01) |
| C09B 57/00 | (2006.01) |
| H01L 51/05 | (2006.01) |

(52) U.S. Cl.
CPC ........ H01L 51/0072 (2013.01); H01L 51/0053 (2013.01); H01L 51/0054 (2013.01); C07D 487/06 (2013.01); C09B 57/001 (2013.01); H01L 51/0558 (2013.01); Y02E 10/549 (2013.01)

(58) Field of Classification Search
CPC .............................. C07D 487/06; C07D 487/22
See application file for complete search history.

(56) References Cited

FOREIGN PATENT DOCUMENTS
| | | |
|---|---|---|
| CN | 101485007 A | 7/2009 |
| CN | 101952988 A | 1/2011 |

OTHER PUBLICATIONS

Riehm, T., et al. "Tetraazaperopyrenes: A New Class of Multifunctional Chromophores." Chem. Eur. J. (2007), vol. 13, pp. 7317-7329.*

Martens, S.C., et al. "Substituent Effects in the Periphery of 2,9-Bis-Aryl-tetraazaperopyrene Dyes." J. Org. Chem. (2011), vol. 76, pp. 609-617.*
"Substituent Effects." (c) Dec. 2009. Available from: < http://www.mhhe.com/physsci/chemistry/carey/student/olc/graphics/carey04oc/ref/ch12substituenteffects.html >.*
International Preliminary Report on Patentability and Written Opinion issued Jul. 19, 2012 in PCT/IB2012/050990.
Susanne C. Martens, et al. "Substituent Effects in the Periphery of 2,9-Bisaryl-tetraazaperopyrene Dyes" Journal of Organic Chemistry, vol. 76, No. 2, Jan. 21, 2011, pp. 609-617.
Till Riehm, et al., "Tetraazaperopyrenes: A New Class of Multifunctional Chromophores" Chem. Eur. J. vol. 16/13, No. 7, 2007, pp. 7317-7329.

* cited by examiner

Primary Examiner — Noble Jarrell
Assistant Examiner — John S Kenyon
(74) Attorney, Agent, or Firm — Oblon, McClelland, Maier & Neustadt, L.L.P.

(57) ABSTRACT

A tetraazaperopyrene compound of formula (I): wherein: $R^1$, $R^2$, $R^3$, $R^4$, $R^5$, $R^6$, $R^7$, $R^8$ at each occurrence, independently are selected from H, Cl and Br, with the proviso that at least one of $R^1$, $R^2$, $R^3$, $R^4$, $R^5$, $R^6$, $R^7$ and $R^8$ is Cl or Br, $R^9$, $R^{10}$, at each occurrence, independently are selected from H, a $C_{1-30}$ alkyl group, a $C_{1-30}$ haloalkyl group, a $C_{6-14}$ aryl group, a heteroaryl group having 5 to 14 ring atoms, and a $C_{7-20}$ arylalkyl group, wherein aryl, heteroaryl and arylalkyl can be optionally substituted with one or more halogen, $C_{1-4}$ haloalkyl, —CN, —NO$_2$, —CHO, —COOH, —CONH$_2$, —CO($C_{1-14}$ alkyl), —COO($C_{1-14}$ alkyl), —CONHC($C_{1-14}$ alkyl) and —CON($C_{1-14}$ alkyl)$_2$ groups.

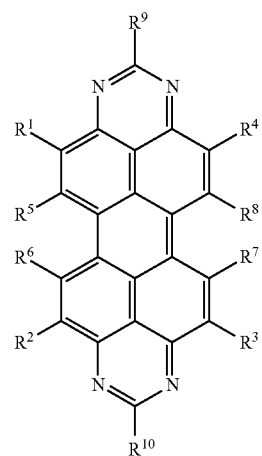

(I)

18 Claims, 8 Drawing Sheets

TETRAAZAPEROPYRENE COMPOUNDS AND THEIR USE AS N-TYPE SEMICONDUCTORS

The invention relates to tetraazaperopyrene compounds and their use as n-type semiconductors.

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semiconductors with high mobility. The performance and stability of organic n-type materials have significantly lagged behind their p-type counterparts. Some challenges for advancing the technology of organic n-type materials include their vulnerability to ambient conditions (e.g., air) and solution-processability. For example, it is desirable for these materials to be soluble in common solvents so that they can be formulated into inks for inexpensive printing processes.

The most common air-stable n-type organic semiconductors include perfluorinated copper phthalocyanine ($CuF_{16}Pc$), fluoroacyl oligothiophenes (e.g., DFCO-4TCO), N,N'-fluorocarbon-substituted naphthalene diimides (e.g., NDI-F, NDI-XF), cyano-substituted perylene diimides (e.g., PDI-FCN$_2$), and cyano-substituted naphthalene diimides (e.g., NDI-8CN$_2$). See, e.g., Bao et al. (1998), *J. Am. Chem. Soc.*, 120: 207-208; de Oteyza et al. (2005), *Appl. Phys. Lett.*, 87: 183504; Schön et al. (2000), *Adv Mater.* 12: 1539-1542; Ye et al. (2005), *Appl. Phys. Lett.*, 86: 253505; Yoon et al. (2006), *J. Am. Chem. Soc.*, 128: 12851-12869; Tong et al. (2006), *J. Phys. Chem. B.*, 110: 17406-17413; Yuan et al. (2004), *Thin Solid Films*, 450: 316-319; Yoon et al. (2005), *J. Am. Chem. Soc.*, 127: 1348-1349; Katz et al. (2000), *J. Am. Chem. Soc.*, 122: 7787-7792; Katz et al. (2000), *Nature* (London), 404: 478-481; Katz et al (2001), *Chem. Phys. Chem.*, 3: 167-172; Jung et al. (2006), *Appl. Phys. Lett.*, 88: 183102; Yoo et al. (2006), *IEEE Electron Device Lett.*, 27: 737-739; Jones et al. (2004), *Angew. Chem., Int. Ed. Engl.*, 43: 6363-6366; and Jones et al. (2007), *J. Am. Chem. Soc.*, 129: 15259-15278.

Accordingly, given potential applications in inexpensive and large-area organic electronics that can be produced by high-throughput reel-to-reel manufacture, the art desires new organic n-type semiconducting compounds, especially those possessing desirable properties such as air stability, high charge transport efficiency, and good solubility in common solvents.

Tetraazaperopyrenes having no core substitution are described in a) T. Riehm, *Dissertation*, Universität Heidelberg, 2008; b) T. Riehm, G. De Paoli, A. E. Konradsson, L. De Cola, H. Wadepohl, L. H. Gade, *Chem.-Eur. J.* 2007, 13, 7317, and c) S. C. Martens, T. Riehm, S. Geib, H. Wadepohl and L. H. Gade, *J. Org. Chem.* 2011, 76, 609-617.

In light of the foregoing, it is an object of the present invention to provide compounds that can be utilized as organic semiconductors and related materials, compositions, composites, and/or devices that can address various deficiencies and shortcomings of the state-of-the-art, including those outlined above.

The object is solved by tetraazapyrene compounds of formula I:

(I)

wherein:
$R^1, R^2, R^3, R^4, R^5, R^6, R^7, R^8$ at each occurrence, independently are selected from H, Cl and Br, with the proviso that at least one of $R^1, R^2, R^3, R^4, R^5, R^6, R^7$ and $R^8$ is Cl or Br, $R^9$, $R^{10}$, at each occurrence, independently are selected from H, a $C_{1-30}$ alkyl group, a $C_{1-30}$ haloalkyl group, a $C_{6-14}$ aryl group, a heteroaryl group having 5 to 14 ring atoms, and a $C_{7-20}$ arylalkyl group, wherein aryl, heteroaryl and arylalkyl can be optionally substituted with one or more halogen, $C_{1-4}$ haloalkyl, —CN, —NO$_2$, —CHO, —COOH, —CONH$_2$, —CO($C_{1-14}$ alkyl), —COO($C_{1-14}$ alkyl), —CONHC($C_{1-14}$ alkyl) and —CON($C_{1-14}$ alkyl)$_2$ groups.

It has been found that the core-halogenated tetraazaperopyrene compounds of the present invention have semiconducting activity. Materials prepared from these compounds have demonstrated unexpected properties. It has been discovered that compounds of the present invention can have high carrier mobility and/or good current modulation characteristics in field-effect devices (e.g., thin-film transistors). In addition, it has been discovered that compounds of the present invention can possess certain processing advantages compared to related representative compounds such as better solubility to permit solution-processability and/or good stability at ambient conditions, for example, air stability. Further, the compounds can be embedded with other components for utilization in a variety of semiconductor-based devices.

$R^9$ and $R^{10}$ can be a $C_{1-30}$ alkyl group. As used herein, "alkyl" refers to a straight-chain or branched saturated hydrocarbon group. Examples of alkyl groups include methyl, ethyl, propyl (e.g., n-propyl and isopropyl), butyl (e.g., n-butyl, isobutyl, s-butyl, t-butyl), pentyl groups (e.g., n-pentyl, isopentyl, neopentyl), and hexyl (e.g., n-hexyl). An alkyl group can have 1 to 30 carbon atoms, for example 1 to 20 carbon atoms (i.e., $C_{1-20}$ alkyl group). A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl).

$R^9$ and $R^{10}$ can be a $C_{1-30}$ haloalkyl group. As used herein, "haloalkyl" refers to an alkyl group having one or more halogen substituents. A haloalkyl group can have 1 to 30 carbon atoms, for example 1 to 10 carbon atoms (i.e., $C_{1-10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula —$C_aH_{2a+1-b}X_b$, wherein X, at each occurrence, is F, Cl, Br, or I, a is an integer in the range of 1 to 20, and b is an integer in the range of 1 to 41, provided that b is not greater than 2a+1.

Preferred haloalkyl groups are $C_{1-6}$ haloalkyl groups, in particular $C_{1-4}$ haloalkyl groups. Particularly preferred are haloalkyl groups containing one ore more fluorine substituents. Examples of particular haloalkyl groups are —$CF_3$, —$C_2F_5$, —$C_3F_7$, —$C_4F_9$ and —$CH_2C_3F_7$.

$R^9$ and $R^{10}$ can be an aryl group having from 6 to 14 carbon atoms. As used herein, "aryl" refers to an aromatic monocyclic hydrocarbon ring system or a polycyclic ring system in which two or more aromatic hydrocarbon rings are fused together or at least one aromatic monocyclic hydrocarbon ring is fused to one or more cycloalkyl and/or cycloheteroalkyl rings. Examples of aryl groups having only aromatic carbocyclic ring(s) include, but are not limited to, phenyl, 1-naphthyl, 2-naphthyl, anthracenyl, phenanthrenyl and like groups. Examples of polycyclic ring systems in which at least one aromatic carbocyclic ring is fused to one or more cycloalkyl or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In certain embodiments, the aryl group is an aryl group substituted with another aryl group and can be referred to as a biaryl group. Examples of biaryl groups are a biphenyl group and a terphenyl group. In certain embodiments, the aryl group is a phenyl group.

$R^9$ and $R^{10}$ can be aryl groups, as defined above, substituted with one or more, e.g. 1 to 5 electron-withdrawing group independently selected from halogen, —CN, —$NO_2$, —$CF_3$, —$OCF_3$, —$CO_2(C_{1-14}$ alkyl), —CHO, $C_1$-$C_{14}$ alkylsulfon, $C_{6-14}$ arylsulfon, a sulfonic acid $C_{1-14}$ alkylester or —$C_{6-14}$ arylester group, —CONH($C_{1-14}$ alkyl) and —CON($C_{1-14}$ alkyl)$_2$. In some preferred embodiments, the electron withdrawing group is halogen, —COO($C_{1-14}$ alkyl), —CN, —$NO_2$, —$CF_3$, or —$OCF_3$. In certain embodiments, the electron withdrawing group is F, Cl, Br, I, or —CN.

In certain embodiments, the aryl group is a phenyl group substituted with 1 to 5 halogen atoms. In some preferred embodiments, $R^9$, $R^{10}$ is a phenyl group substituted with 1 to 5 F atoms. In some embodiments, the aryl group is perhalogenated, i.e. all of the hydrogen atoms are replaced with halogen atoms, in particular with F atoms. One preferred perhalogenated aryl group is pentafluorophenyl.

$R^9$ and $R^{10}$ can be arylalkyl groups having from 7 to 20 carbons atoms. The aryl group bound in the arylalkyl group can be an (optionally substituted) aryl group having from 6 to 14 carbon atoms, as defined herein, linked via an alkylene group, in general an $C_{1-6}$ alkylene group, to the tetraazapyrene core. Examples of arylalkyl groups are benzyl, phenylethyl and phenylpropyl.

$R^9$ and $R^{10}$ can be an arylalkyl group substituted with one or more electron withdrawing groups selected from halogen, —COO($C_{1-14}$ alkyl), —CN, —$NO_2$, —$CF_3$, or —$OCF_3$. In certain embodiments, the electron withdrawing group is F, Cl, Br, I, or —CN, in particular F. The arylalkyl group can be perhalogenated, i.e. all of the hydrogen atoms are replaced with halogen atoms, in particular with F atoms.

$R^9$ and $R^{10}$ can be a heteroaryl group having 5 to 14 ring atoms. As used herein, "heteroaryl" refers to an aromatic monocyclic ring system containing at least one ring heteroatom selected from O, N, S, Si, and Se or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have from 5 to 14 ring atoms (e.g., 5-14 membered heteroaryl group) and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

where T is O, S, NH, N-alkyl, N-aryl, N-(arylalkyl) (e.g., N-benzyl), $SiH_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

The chloro- or bromo-substituted tetraazapyrenes can be obtained from the tetraazapyrenes of formula (II) by chlorination or bromination using a chlorination or bromination agent.

(II)

Preferably, $R^5$, $R^6$, $R^7$ and $R^8$ in formula (I) are hydrogen.

In one preferred embodiment, $R^1$, $R^2$, $R^3$ and $R^4$ are Cl or Br. The tetrahalogenated tetraazaperopyrenes can be obtained from the tetraazapyrenes of formula (II) using as chlorination agent N,N'-dichloroisocyanuric acid and as bromination agent N,N'-dibromoisocyanuric acid, according to Reaction Scheme a:

(II)

Brominated tetraazaperopyrenes can also be obtained by using molecular bromine in concentrated sulfuric acid as the bromination agent.

$FeCl_3$ and $FeBr_3$, respectively, can be added as catalysts.

2,7-substituted tetraazapyrenes of formula (II) can be obtained by reacting 4,9-diaminoperylenequinone-3,10-diimine (III) and an carboxylic acid chloride containing residue $R^9$ or $R^{10}$ according to Reaction Scheme b:

(III)

The synthesis of compounds of formula (II) for a variety of different $R^9$ is described in a) T. Riehm, Dissertation, Universität Heidelberg, 2008; b) T. Riehm, G. De Paoli, A. E. Konradsson, L. De Cola, H. Wadepohl, L. H. Gade, Chem.-Eur. J. 2007, 13, 7317, and c) S. C. Martens, T. Riehm, S. Geib, H. Wadepohl and L. H. Gade, J. Org. Chem. 2011, 76, 609-617.

Suitable carboxylic acid anhydrides are e.g. pentafluorobenzoic acid chloride and perfluoroalkane carboxylic acid chlorides containing perfluoroalkyl groups with 1 to 6 carbon atoms.

Compound (III) can be synthesized as described in a) L. H. Gade, C. H. Galka, K. W. Hellmann, R. M. Williams, L. De Cola, I. J. Scown, M. McPartlin, Chem.-Eur. J. 2002, 8, 3732.

Aryl-substituted tetraazapyrenes can be obtained form chloro- or bromo-substituted tetraazapyrenes by substitution of chlorine or bromine using the corresponding arylboronic acid, such as phenylboronic acid.

As the compounds disclosed herein are soluble in common solvents, the present invention can offer processing advantages in fabricating electrical devices such as thin film semiconductors, field-effect devices, organic light emitting diodes (OLEDs), organic photovoltaics, photodetectors, capacitors, and sensors. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

Accordingly, the present invention further provides compositions that include one or more compounds disclosed herein dissolved or dispersed in a liquid medium, for example, an organic solvent, water or ionic liquids, or combinations thereof. In some embodiments, the composition can further include one or more additives independently selected from detergents, dispersants, binding agents, compatiblizing agents, curing agents, initiators, humectants, antifoaming agents, wetting agents, pH modifiers, biocides, and bacteriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, such compositions can include one or more compounds disclosed herein, for example, two or more different compounds of the present invention can be dissolved in an organic solvent to prepare a composition for deposition. In certain embodiments, the composition can include two or more regioisomers. Further, it should be understood that the devices described herein also can comprise one or more compounds of the present invention, for example, two or more regioisomers as described herein.

Various deposition techniques, including various solution-processing techniques, have been used in preparing organic electronics. For example, much of the printed electronics technology has focused on inkjet printing, primarily because this technique offers greater control over feature position and multilayer registration. Inkjet printing is a non-contact process, which offers the benefits of not requiring a preformed master (compared to contact printing techniques), as well as digital control of ink ejection, thereby providing drop-on-demand printing. Micro dispensing is another non-contact method of printing. However, contact printing techniques have the key advantage of being well-suited for very fast roll-to-roll processing. Exemplary contact printing techniques include, but are not limited to, screen-printing, gravure printing, offset printing, flexographic printing, lithographic printing, pad printing, and microcontact printing. As used herein, "printing" includes a noncontact process, for example, inkjet printing, micro dispensing, and the like, and a contact process, for example, screen-printing, gravure printing, offset printing, flexographic printing, lithographic printing, pad printing, micro-contact printing, and the like. Other solution processing techniques include, for example, spin coating, drop-casting, zone casting, dip coating, blade coating, or spraying. In addition, the deposition step can be carried out by vacuum vapor-deposition.

The present invention, therefore, further provide methods of preparing a semiconductor material. The methods can include preparing a composition that includes one or more compounds disclosed herein dissolved or dispersed in a liquid medium such as a solvent or a mixture of solvents, and depositing the composition on a substrate to provide a semiconductor material (e.g., a thin film semiconductor) that includes one or more compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatiblizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds and the semiconductor materials disclosed herein also as well as methods of making the same are within the scope of the present invention.

Accordingly, the present invention provides articles of manufacture such as the various devices described herein that include a composite having a semiconductor material of the present invention, a substrate component, and/or a dielectric component. The substrate component can be selected from materials including doped silicon, an indium tin oxide (ITO), ITO-coated glass, ITO-coated polyimide or other plastics, aluminum or other metals alone or coated on a polymer or other substrate, a doped polythiophene or other polymers, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), and hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be incorporated within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

An aspect of the present invention, therefore, relates to methods of fabricating an organic field effect transistor that incorporates a semiconductor material of the present invention. The semiconductor materials of the present invention can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present compounds on doped silicon substrates, using $SiO_2$ as the dielectric, in top-contact geometries. In particular embodiments, the active semiconducting layer which incorporates at least a compound of the present invention can be deposited by vacuum vapor deposition at room temperature or at an elevated temperature. In other embodiments, the active semiconducting layer which incorporates at least a compound of the present invention can be applied by solution-based process, for example, spin-coating or jet printing. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present invention can be deposited at room temperature or at an elevated temperature. In other embodiments, the active semiconducting layer which incorporates at least a compound of the present invention can be applied by spin-coating or printing as described herein. Gate and source/drain contacts can be made of Au, other metals, or conducting polymers and deposited by vapor-deposition and/or printing.

Other articles of manufacture in which compounds of the present invention are useful are photovoltaics or solar cells. Compounds of the present invention can exhibit broad optical absorption and/or a very positively shifted reduction potential making them desirable for such applications. Accordingly, the compounds described herein can be used as an n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present invention in such devices is within the knowledge of the skilled artisan.

Accordingly, another aspect of the present invention relates to methods of fabricating an organic light-emitting transistor, an organic light-emitting diode (OLED), or an organic photovoltaic device that incorporates one or more semiconductor materials of the present invention.

The following examples are provided to illustrate further and to facilitate understanding of the present invention and are not in any way intended to limit the invention.

EXAMPLES

Example 1

Synthesis of tetraazaperopyrene (TAPP) and its 2,9-disubstituted derivatives

TAPP derivative

R = Alkyl
Aryl
Heteroaryl

The parent compound, 1,3,8,10-tetraazaperopyrene, was prepared by treating DPDI with triethyl orthoformate in the presence of catalytic amounts of formic acid and purified by sublimation in high vacuum. The elemental analysis is consistent with its formulation as $C_{22}H_{10}N_4$. The yellow-brown compound is only sparingly soluble in organic solvents, but readily dissolves in $H_2SO_4$. Solutions of the N-deuterated tetracation were characterized by $^1H$ and $^{13}C$ NMR spectroscopy. 2,9-Disubstituted derivatives are readily accessible by treating DPDI either with the corresponding carboxylic acid chloride or anhydride (2 mol equiv) in the presence of triethylamine in THF or with a large excess of acid chloride or anhydride in nitrobenzene at reflux.

Example 2

Synthesis of 4,7,11,14-tetrachloro-1,3,8,10-tetraazaperopyrene

To a solution of 100 mg (0.3 mmol) tetraazaperopyrene in 10 ml concentrated sulfuric acid were added in the dark 360 mg (1.8 mmol) dichloroisocyanuric acid and the reaction mixture stirred for 7 days at 100° C. The reaction mixture was cooled to room temperature, poured on ice and neutralized with aqueous NaOH. The precipitate was filtered, washed with water and repeatedly extracted with dichloromethane until the solution was colourless. The solvent was removed in vacuo, the residue re-crystallized from THF, washed with pentane and dried in vacuo. The product was isolated as an ochre coloured solid with a yield of 16% (23 mg, 0.05 mmol).

$^1$H-NMR (399.89 MHz, CDCl$_3$, 295 K):
δ=10.33 (s, 2H, C1H), 9.86 (s, 4H, C3H).

Example 3

General Experimental Procedure for the Synthesis of 2,9-disubstituted tetraazaperopyrenes To a solution of the 2,9-disubstituted tetraazaperopyrene in concentrated sulfuric acid, dichloroisocyanuric acid (DIC) was added and the reaction mixture stirred for 3 days at 35° C. The reaction mixture was cooled to room temperature, the magenta coloured reaction mixture poured on ice, and the precipitate washed with water. The precipitate was extracted with dichloromethane until the solution was colourless. The solvent was removed in vacuo, the residue recrystallized from THF, washed with pentane and dried in vacuo.

Example 4

Synthesis of 2,9-bis-(trifluoromethyl)-4,7,11,14-tetrachloro-1,3,8,10-tetraazaperopyrene According to the general procedure, 110 mg (0.24 mmol) of 2,9-bis-(trifluormethyl)-1,3,8,10-tetraazaperopyrene in 10 ml concentrated sulfuric acid were reacted with 260 mg (1.3 mol) DIC. The product was obtained as orange solid in a yield of 55% (80 mg, 0.13 mmol).

$^1$H-NMR (399.89 MHz, CDCl$_3$, 295 K):
δ=9.95 (s, 4H, CH).
$^{19}$F-NMR (376.27 MHz, CDCl$_3$, 295 K)
δ=−68.42 (s, 6F).

Example 5

Synthesis of 2,9-bis-(pentafluoroethyl)-4,7,11,14-tetrachloro-1,3,8,10-tetraazaperopyrene According to the general procedure 80 mg (0.14 mmol) of 2,9-bis-(pentafluoroethyl)-1,3,8,10-tetraazaperopyrene in 10 ml concentrated sulfuric acid and were reacted with 145 mg (0.73 mmol) DIC. The product was obtained as red solid in a yield of 43% (42 mg, 0.06 mmol).

$^1$H-NMR (600.13 MHz, CDCl$_3$, 295 K):
δ=9.95 (s, 4H, CH).
$^{19}$F-NMR (376.27 MHz, CDCl$_3$, 295 K)
δ=−81.4 (s, 6F, CF$_3$), −114.9 (s, 4F, CF$_2$).

Example 6

Synthesis of 2,9-bis-(heptafluoropropyl)-4,7,11,14-tetrachloro-1,3,8,10-tetraazaperopyrene According to the general experimental procedure 70 mg (0.11 mmol) of 2,9-bis-(heptafluoropropyl)-4,7,11,14-tetrachloro-1,3,8,10,-tetraazaperopyrene in 10 ml concentrated sulfuric acid were reacted with 120 mg (0.61 mmol) DIC. The product was obtained as orange solid in a yield of 66% (55 mg, 0.07 mmol).

$^1$H-NMR (399.89 MHz, d8-THF, 295 K):
δ=10.47 (s, 4H, CH).
$^{19}$F-NMR (376.27 MHz, d8-THF, 295 K)
δ=−80.9 (t, 6F, $^3J_{FF}$=9.2 Hz, CF$_3$), −113.6 (guar, 4F, $^3J_{FF}$=9.1 Hz, CF$_2$), −126.0 (s, 4F, CF$_2$).

Example 7

Synthesis of 2,9-bis-(nonafluorobutyl)-4,7,11,14-tetrachloro-1,3,8,10-tetraazaperopyrene According to the general experimental procedure 35 mg (0.05 mmol) of 2,9-bis-(nonafluorobutyl)-1,3,8,10-tetraazaperopyrene in 5 ml concentrated sulfuric acid were reacted with 52 mg (0.26 mmol) DIC. The product was obtained as orange solid in a yield of 40% (18 mg, 0.02 mmol).

$^1$H-NMR (600.13 MHz, d8-THF, 295 K):
δ=10.43 (s, 4H, CH).
$^{19}$F-NMR (376.27 MHz, d8-THF, 295 K)
δ=−81.8 (m, 6F, CF$_3$), −112.8 (m, 4F, CF$_2$), −122.2 (m, 4F, CF$_2$), −125.9 (m, 4F, CF$_2$).

Example 8

Synthesis of 2,9-bis-(pentafluorophenyl)-4,7,11,14-tetrochloro-1,3,8,10-tetraazaperopyrene According to the general procedure 85 mg (0.13 mmol) of 2,9-bis-(2,3,4,5,6-pentafluorophenyl)-1,3,8,10-tetraazaperopyrene in 10 ml concentrated sulfuric acid were reacted with 260 mg (1.3 mmol) DIC. The product was obtained as yellow solid in a yield of 85% (88 mg, 0.11 mmol).

$^1$H-NMR (399.89 MHz, CDCl$_3$, 295 K):
δ=9.89 (s, 4H, CH).
$^{19}$F-NMR (376.27 MHz, CDCl$_3$, 295 K)
δ=−142.0 (m, 4F), −151.6 (m, 2F), −161.1 (m, 4F).

Example 9

General procedure for the preparation of fourfold phenyl-substituted TAPPs:

An oven-dried Schlenk tube was equipped with 100 mg (0.1 mmol) 2,9-bis-heptafluoropropyl-4,7,11,14-tetrabromo-1,3,8,10-tetraazaperopyrene, 0.6 mmol of the corresponding phenylboronic acid derivative, 7.3 mg (0.01 mmol) Pd(dppf)Cl$_2$ and 228 mg (0.7 mmol) Cs$_2$CO$_3$ and evacuated and filled with argon for three times. 25 ml abs. 1,4-dioxane were added and the resulting mixture was stirred at 101° C. for 48 hours. Then, the reaction mixture was directly dispersed on Celite and purified by column chromatography (pentane-ethyl acetate, 2:1) to yield the product as a solid.

Example 9a

Synthesis of 2,9-bis-trifluoromethyl-4,7,11,14-tetrabromo-1,3,8,10-tetraazaperopyrene Yield: 803 mg (1.02 mmol, 51%)
$^1$H NMR (600.13 MHz, THF-d$_8$): δ=10.67 (s, 4H).
$^{19}$F NMR (376.23 MHz, THF-d$_8$): δ=−68.76 (s, 6F, CF$_3$).

Example 9b

Synthesis of 2,9-bis-pentafluoroethyl-4,7,11,14-tetrabromo-1,3,8,10-tetraazaperopyrene Yield: 1320 mg (1.50 mmol, 75%)
$^1$H NMR (600.13 MHz, THF-d$_8$): δ=10.68 (s, 4H).
$^{19}$F NMR (376.23 MHz, THF-d$_8$): δ=−82.32 (m, 6F, CF$_3$), −115.24 (m, 4F, CF$_2$).

Example 9c

Synthesis of 2,9-bis-heptafluoropropyl-4,7,11,14-tetrabromo-1,3,8,10-tetraazaperopyrene Yield: 971 mg (0.97 mmol, 50%)
$^1$H NMR (600.13 MHz, THF-d$_8$): δ=10.68 (s, 4H).
$^{19}$F NMR (376.23 MHz, THF-d$_8$): δ=−80.93 (t, 6F, $^3J_{FF}$=9.1 Hz, CF$_3$), −113.60 (m, 4F, CF$_2$), −125.98 (m, 4F, CF$_2$).

Example 10

Synthesis of 2,9-bis-nonafluorobutyl-4,7,11,14-tetrabromo-1,3,8,10-tetraazaperopyrene Yield: 1476 mg (1.36 mmol, 69%)

$^1$H NMR (600.13 MHz, THF-$d_8$): δ=10.65 (s, 4H).

$^{19}$F NMR (376.23 MHz, THF-$d_8$): δ=−81.77 (t, 6F, $^3J_{FF}$=10.0 Hz, CF$_3$), −112.79 (m, 4F, CF$_2$), −122.19 (m, 4F, CF$_2$), −125.87 (m, 4F, CF$_2$)

Example 11

General procedure for the preparation of fourfold phenyl-substituted TAPPs:

An oven-dried Schlenk tube was equipped with 100 mg (0.1 mmol) 2,9-bis-heptafluoropropyl-4,7,11,14-tetrabromo-1,3,8,10-tetraazaperopyrene, 0.6 mmol of the corresponding phenylboronic acid derivative, 7.3 mg (0.01 mmol) Pd(dppf)Cl$_2$ and 228 mg (0.7 mmol) Cs$_2$CO$_3$ and evacuated and filled with argon for three times. 25 ml abs. 1,4-dioxane were added and the resulting mixture was stirred at 101° C. for 48 hours.

Then, the reaction mixture was directly dispersed on Celite and purified by column chromatography (pentane-ethyl acetate, 2:1) to yield the product as a solid.

Example 11a

Synthesis of 2,9-bis-heptafluoropropyl-4,7,11,14-tetra-4-trifluoromethylphenyl-1,3,8,10-tetraazaperopyrene

Example 12

Synthesis of 2,9-bis-heptafluoropropyl-4,7,11,14-tetrapyrenyl-1,3,8,10-tetraazaperopyrene An oven-dried Schlenk tube was brought into a glove box and equipped with 100 mg (0.1 mmol) 2,9-bis-heptafluoropropyl-4,7,11,14-tetrabromo-1,3,8,10-tetraazaperopyrene, 200 mg (0.8 mmol) pyreneboronic acid, 10 mg (0.01 mmol) Pd$_2$(dba)$_3$, 2 mg (0.015 mmol) P($^t$Bu)$_3$ and 325 mg (1.0 mmol) Cs$_2$CO$_3$. 25 ml abs. 1,4-dioxane were added and the resulting mixture was stirred at 101° C. for 48 hours. Then, the reaction mixture was directly dispersed on Celite and purified by column chromatography (pentane-ethyl acetate, 2:1) to yield the product as a dark green solid.

Yield: 49 mg (0.03 mmol, 30%) of a dark green solid.

$^1$H NMR (600.13 MHz, THF-$d_8$): δ=10.63 (m, 4H, CH), 8.51-7.97 (m, 36H, C$^{Pyrene}$H).

$^{19}$F NMR (376.23 MHz, THF-$d_8$): δ=−81.21 (t, 6F, $^3J_{FF}$=9.2 Hz, CF$_3$), −114.00 (m, 4F, CF$_2$), −126.27 (m, 4F, CF$_2$).

Example 13

Fabrication of Vapor-Deposited OFETs

Figure 1:
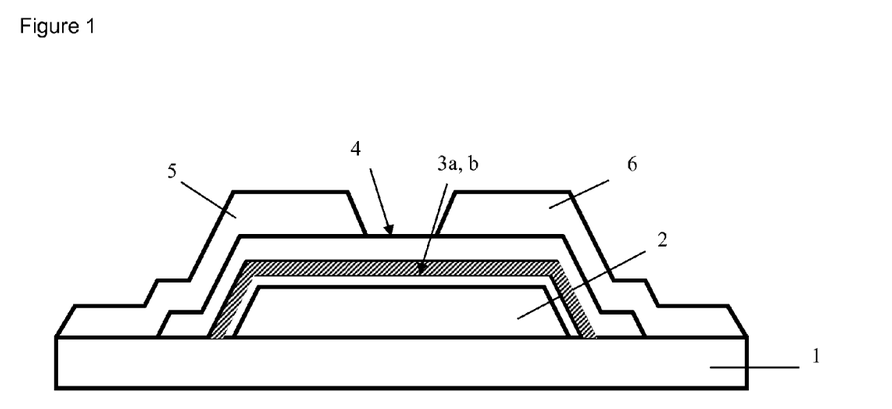

General Procedure for the Fabrication of Vapor-Deposited OFETs in the Top-Contact Configuration FIG. 1 shows the configuration of a TFT with a thin film dielectric using substrate A.

Figure 2:
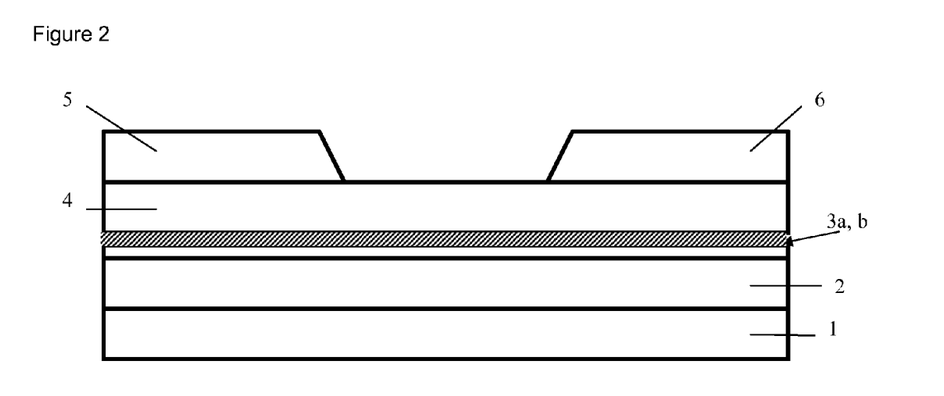

FIG. 2 shows the configuration of a TFT with a thick film dielectric using substrate B.

Highly doped p-type silicon (100) wafers (1) (0.01-0.02 Ω·cm) were used as substrates A. Highly doped p-type silicon (100) wafers (1) (0.005-0.02 Ω·cm) with a 100 nm thick thermally grown SiO$_2$ layer (2) (capacitance 34 nF/cm$^2$) were used as substrates B.

Onto substrates A, a 30 nm thick layer of aluminum (2) is deposited by thermal evaporation in a Leybold UNIVEX 300 vacuum evaporator from a tungsten wire, at a pressure of 2×10$^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) (3b) of phosphonic acid molecules on the aluminum oxide surface (3a). The substrate is taken out of the solution and rinsed with pure 2-propanol, dried in a stream of nitrogen and left for 10 min on a hotplate at a temperature of 100° C. The total capacitance of the AlO$_x$/SAM gate dielectric on substrate A is 810 nF/cm$^2$ in case of C$_{14}$H$_{29}$PO(OH)$_2$ and 710 nF/cm$^2$ in case of C$_7$F$_{15}$C$_{11}$H$_{22}$PO(OH)$_2$.

On substrates B, an about 8 nm thick layer of Al$_2$O$_3$ (3a) is deposited by atomic layer deposition in a Cambridge NanoTech Savannah (80 cycles at a substrate temperature of 250° C.). The surface of the aluminum oxide layer is activated by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) (3b) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the $SiO_2/AlO_x/SAM$ gate dielectric on substrate B is 32 nF/cm$^2$ (independent on the choice of the phosphonic acid).

The contact angle of water on the TDPA-treated substrates is 108°, and on the FOD-PA-treated substrates 118°.

A 30 nm thick film of the organic semiconductor (4) is deposited by thermal sublimation in a Leybold UNIVEX 300 vacuum evaporator from a molybdenum boat, at a pressure of $2 \times 10^{-6}$ mbar and with an evaporation rate of 0.3 nm/s. For the source and drain contacts (5) and (6) 30 nm of gold is evaporated through a shadow mask in a Leybold UNIVEX 300 vacuum evaporator from tungsten boat, at a pressure of $2 \times 10^{-6}$ mbar and with an evaporation rate of 0.3 nm/s. The transistors have a channel length (L) ranging from 10 to 100 μm and a channel width (W) ranging from 50 to 1000 μm. To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage ($V_{DS}$) is held to 3 V (in case of substrate A) or 40 V (in case of substrate B). The gate-source voltage $V_{GS}$ is swept at medium speed from 0 to 3 V in steps of 0.03 V (substrate A) or from 0 to 40 V in steps of 0.4 V (substrate B) and back. The charge-carrier mobility is extracted in the saturation regime from the slope of $(I_D)^{1/2}$ versus $V_{GS}$.

To obtain the output characteristics the drain-source voltage ($V_{DS}$) is swept at medium speed from 0 to 3 V in steps of 0.03 V (substrate A) and from 0 to 40 V in steps of 0.4 V (substrate B), while the gate-source voltage $V_{GS}$ is held at up to 8 different voltages (e.g. 0, 0.5, 1, 1.5, 2, 2.5, 3 V in case of substrate A or 0, 10, 20, 30, 40 V in case of substrate B). The results are summarized in table 1.

Figure 3:
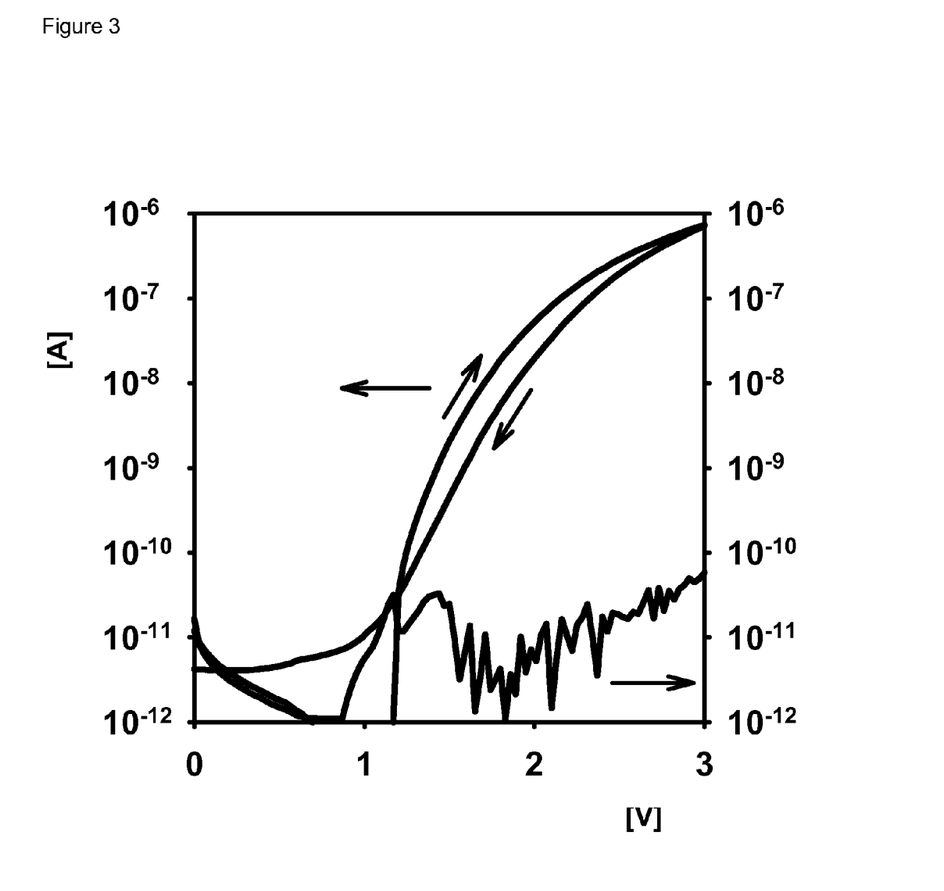
Figure 4:
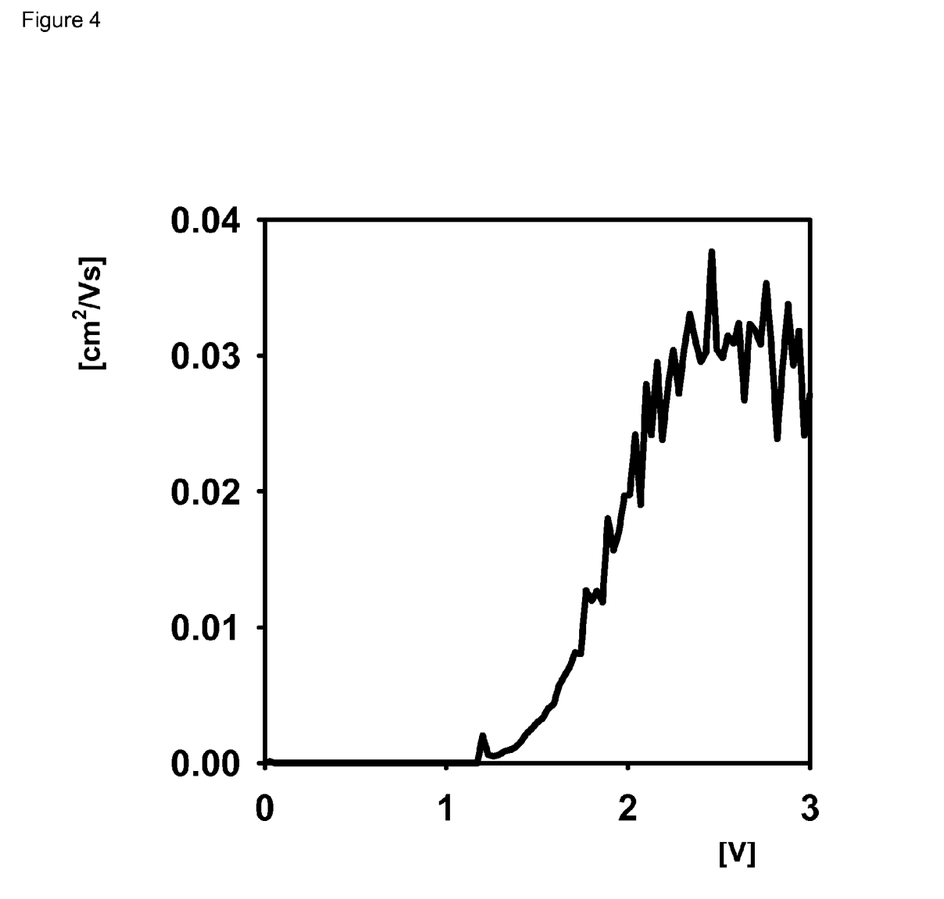
Figure 5:
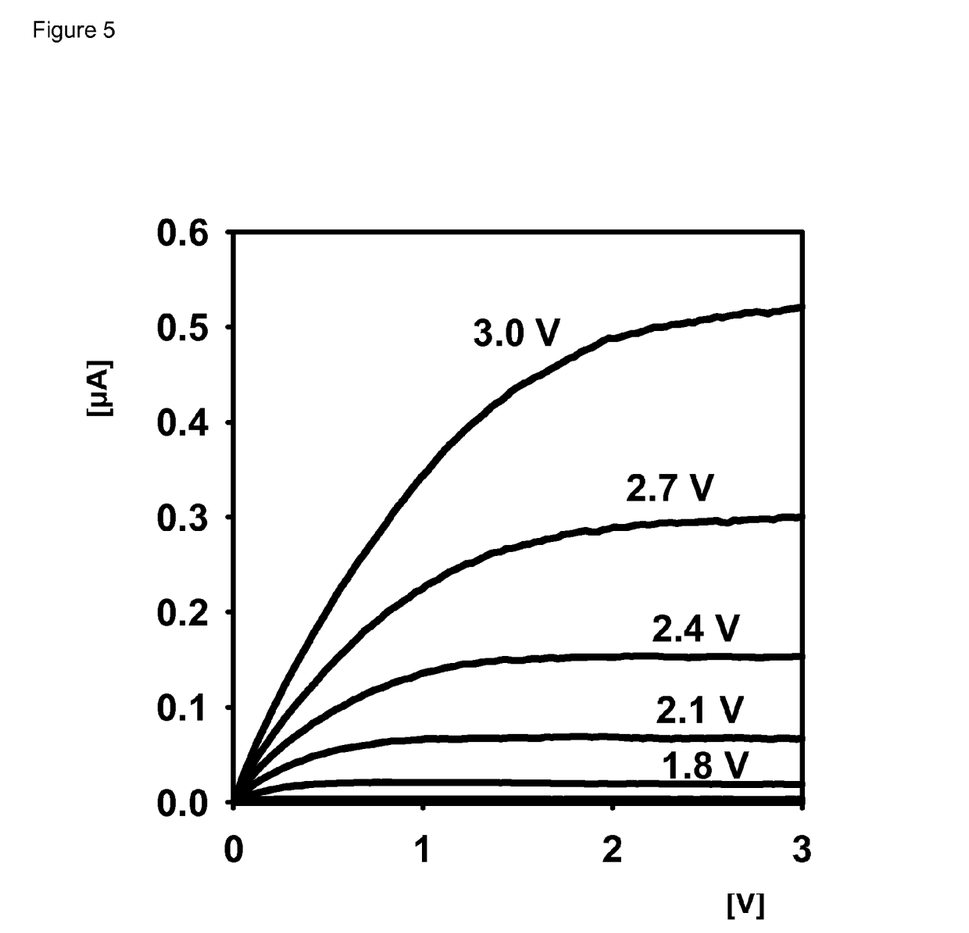

FIGS. 3, 4, 5 show the output characteristics and transfer curve of the compound of Example 6 in a TFT with thin gate dielectric (substrate A). In FIG. 3, the drain current in A is plotted against the gate-source voltage in V. In FIG. 4, the electron mobility in cm$^2$/Vs is plotted against the gate-source voltage in V. The drain-source voltage was 3.0 V. In FIG. 5, the drain current in A is plotted against the drain-source voltage in V. In the gate-source voltage were 3.0 V (uppermost curve), 2.7 V, 2.4 V, 2.1 V and 1.8 V (lowermost curve).

Figure 6:
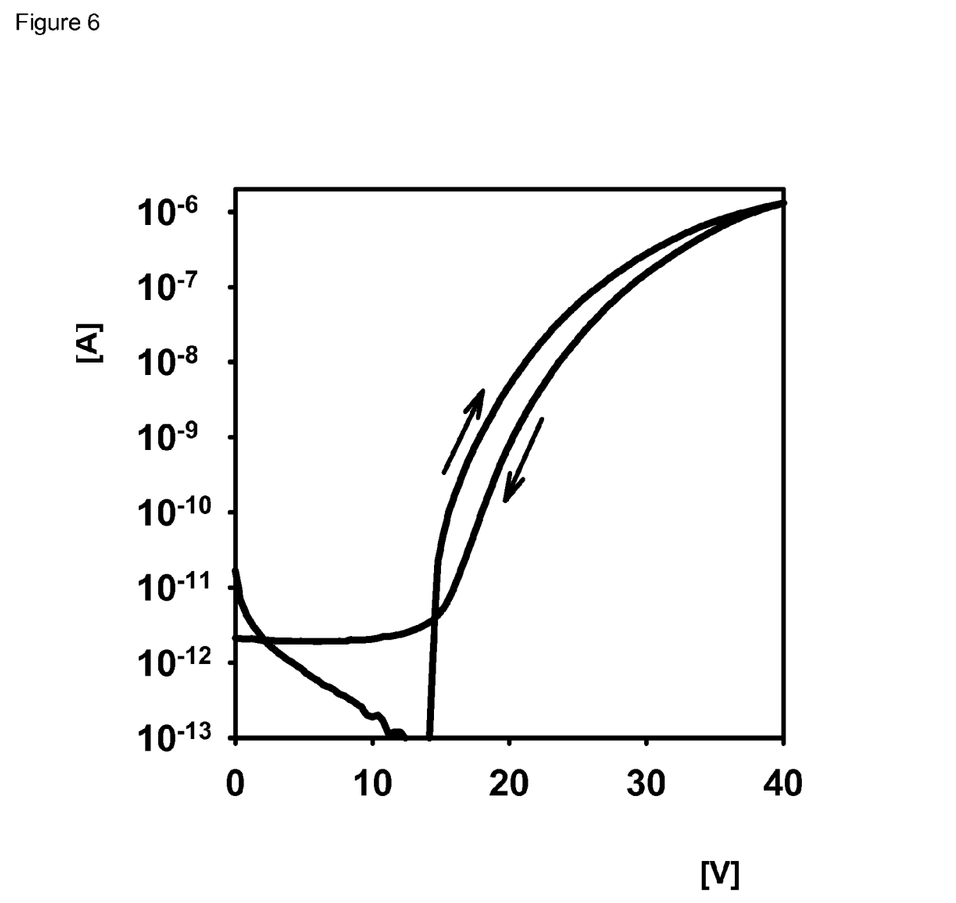
Figure 7:
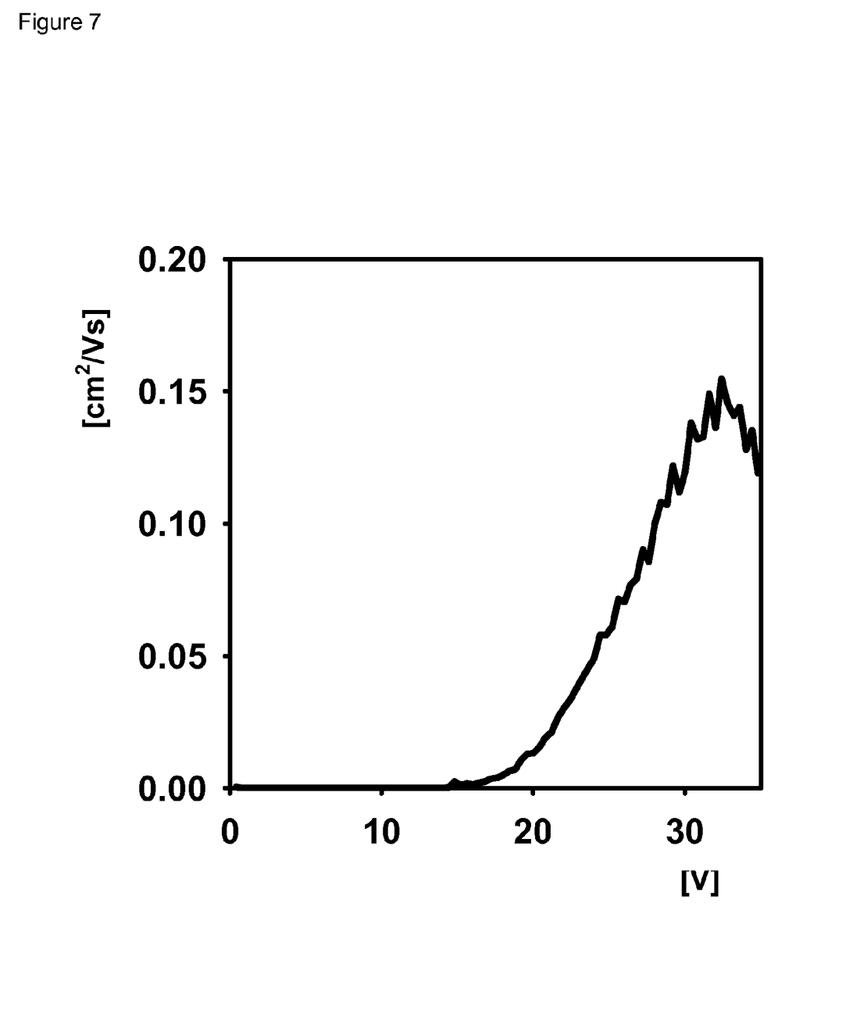
Figure 8:
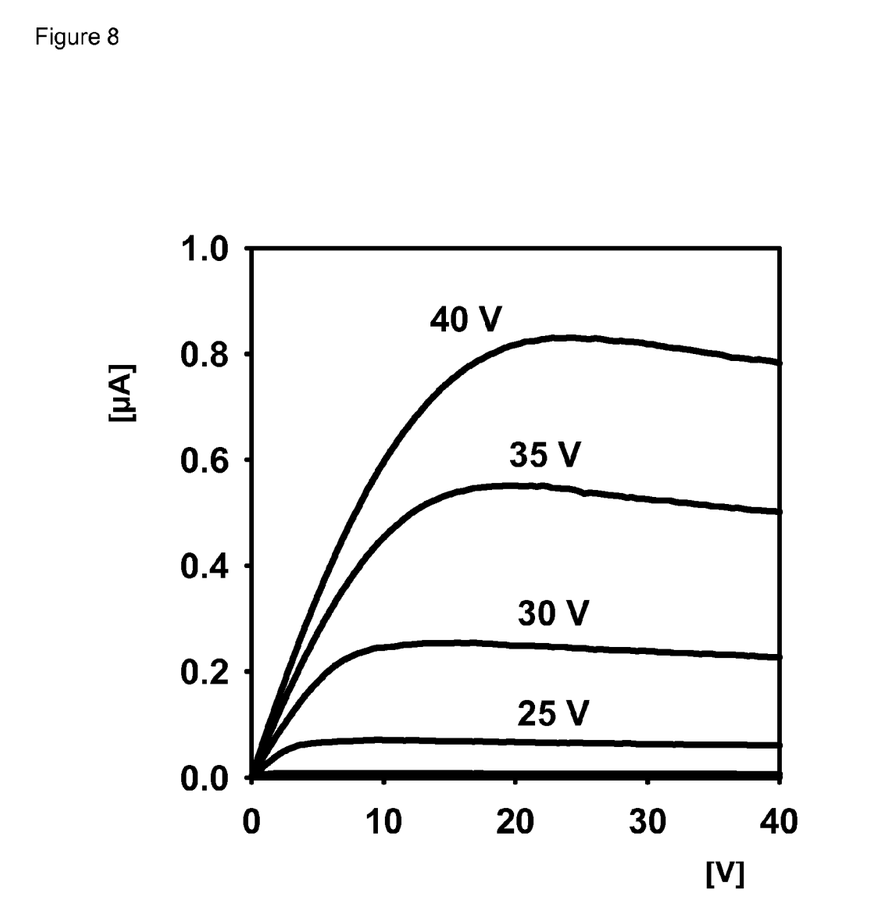
Figure 9:
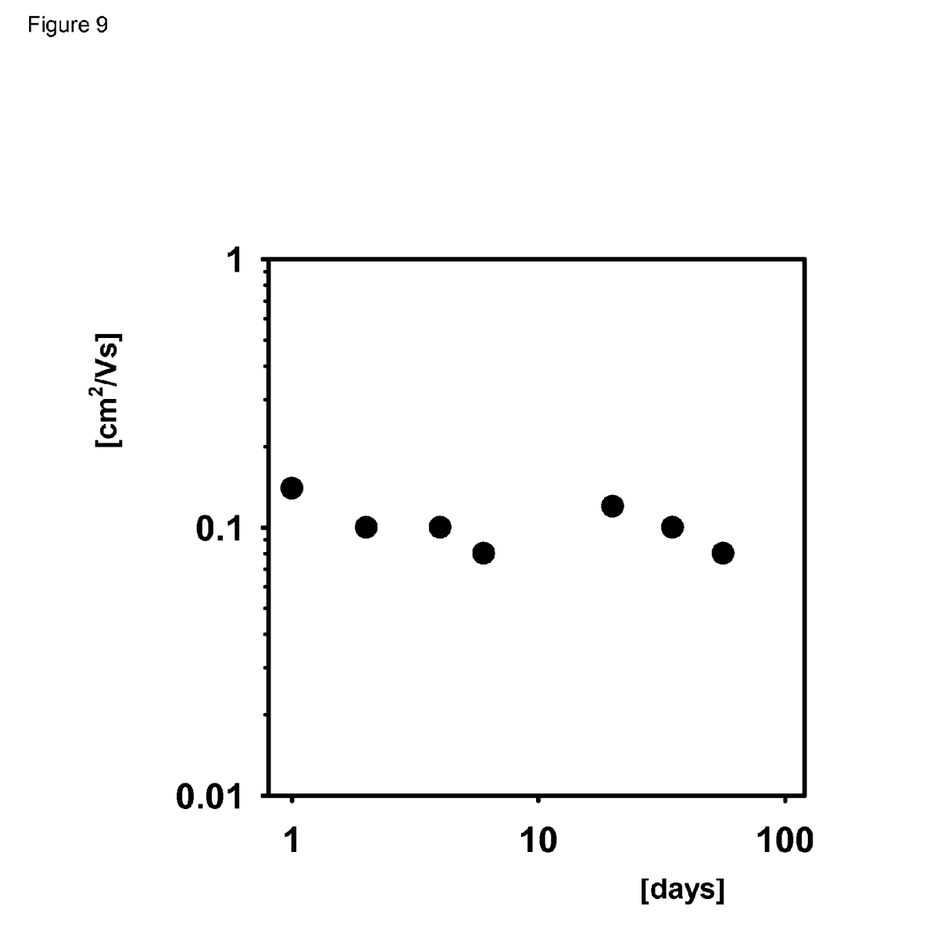

FIGS. 6, 7, 8, 9 show the output characteristics, transfer curve and long term stability of the compound of Example 6 in a TFT with thick gate dielectric (substrate B). In FIG. 6, the drain current in A is plotted against the gate-source voltage in V. In FIG. 7, the electron mobility in cm$^2$/Vs is plotted against the gate-source voltage in V. The drain-source voltage was 40 V. In FIG. 8, the drain current in A is plotted against the drain-source voltage in V. The gate source voltages were 40 V (uppermost curve), 35 V, 30 V and 25 V (lowermost curve). In FIG. 9, the electron mobility in cm$^2$/Vs is plotted against the exposure to air in days.

Table 1 gives the field-effect mobilities (μ) and on/off ratios ($I_{on}/I_{off}$) for compounds of examples 6, 9a, 9b and 9c with a thin (substrate A) and a thick (substrate B) gate dielectric with $C_{14}H_{29}PO(OH)_2$ [TDPA] for the SAM at a certain substrate temperature ($T_{sub}$) measured in ambient air.

| Compound from example | Substrate | Substrate temperature $T_{sub}$ [° C.] | Electron mobility μ [cm$^2$/Vs] | On/off ratio $I_{on}/I_{off}$ |
|---|---|---|---|---|
| 6 | A | 90 | 0.035 | 10$^5$ |
| 6 | B | 90 | 0.14 | 10$^5$ |
| 9a | A | 80 | 0.00038 | 10$^5$ |
| 9b | B | 90 | 0.026 | 5 × 10$^5$ |
| 9c | A | 70 | 0.03 | 5 × 10$^5$ |

The invention claimed is:

1. A tetraazaperopyrene compound of formula (I):

wherein:

R$^1$, R$^2$, R$^3$, R$^4$, R$^5$, R$^6$, R$^7$, and R$^8$ are each independently selected from the group consisting of H, Cl and Br, with the proviso that at least one of R$^1$, R$^2$, R$^3$, R$^4$, R$^5$, R$^6$, R$^7$ and R$^8$ is Cl or Br, R$^9$ and R$^{10}$ are each independently selected from the group consisting of H, a C$_{1-30}$ alkyl group, a C$_{1-30}$ haloalkyl group, a C$_{6-14}$ aryl group, a heteroaryl group having 5 to 14 ring atoms, and a C$_{7-20}$ arylalkyl group, wherein aryl, heteroaryl and arylalkyl can be optionally substituted with one or more halogen, C$_{1-4}$ haloalkyl, —CN, —NO$_2$, —CHO, —COOH, —CONH$_2$, —CO(C$_{1-14}$ alkyl), —COO(C$_{1-14}$ alkyl), —CONHC(C$_{1-14}$ alkyl) and —CON(C$_{1-14}$ alkyl)$_2$ groups.

2. The compound of claim 1, wherein R$^5$, R$^6$, R$^7$ and R$^8$ are H.

3. The compound of claim 1, wherein R$^1$, R$^2$, R$^3$ and R$^4$ are Cl.

4. The compound of claim 1, wherein R$^1$, R$^2$, R$^3$ and R$^4$ are Br.

5. The compound of claim 1, wherein R$^9$ and R$^{10}$ are a C$_{1-10}$ haloalkyl group.

6. The compound of claim 5, wherein R$^9$ and R$^{10}$ are a C$_{1-6}$ perfluoroalkyl group.

7. The compound claim 1, wherein $R^9$ and $R^{10}$ are a $C_{6-14}$ aryl group or a $C_{7-20}$ arylalkyl group which are each substituted with one or more halogen atom.

8. The compound of claim 7, wherein $R^9$ and $R^{10}$ are a phenyl group substituted with 1 to 5 fluorine atoms.

9. A process for producing a compound of formula (I) of claim 1, the process comprising chlorinating or brominating a tetraazaperopyrene of formula (II)

(II)

with a chlorination or bromination agent.

10. The process of claim 9, wherein $R^1$, $R^2$, $R^3$ and $R^4$ are each independently Cl or Br, $R^5$, $R^6$, $R^7$, $R^8$ are H, the chlorination agent is N,N'-dichloroisocyanuric acid, and the bromination agent is N,N'-dibromoisocyanuric acid.

11. The process of claim 9, wherein the tetraazaperopyrene (II) is obtained by reacting 4,9-diaminoperylenquinone-3,10-diimine (III)

(III)

with a carboxylic acid chloride (IV)

(IV)

12. A thin film semiconductor comprising the tetraazaperopyrene of claim 1.

13. A field effect transistor device comprising the thin film semiconductor of claim 12.

14. A photovoltaic device comprising the thin film semiconductor of claim 12.

15. An organic light emitting diode device comprising the thin film semiconductor of claim 12.

16. A unipolar or complementary circuit device comprising the thin film semiconductor of claim 12.

17. The process according to claim 9, comprising chlorinating the tetraazaperopyrene of formula (II) with a chlorination agent.

18. The process according to claim 9, comprising brominating the tetraazaperopyrene of formula (II) with a bromination agent.

* * * * *